(12) United States Patent
Seesselberg

(10) Patent No.: US 10,398,308 B2
(45) Date of Patent: Sep. 3, 2019

(54) APPARATUS FOR DETERMINING AMETROPIA OF AN EYE

(71) Applicant: Carl Zeiss Meditec AG, Jena (DE)

(72) Inventor: Markus Seesselberg, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 357 days.

(21) Appl. No.: 15/207,333

(22) Filed: Jul. 11, 2016

(65) Prior Publication Data

US 2017/0007117 A1    Jan. 12, 2017

(30) Foreign Application Priority Data

Jul. 10, 2015   (DE) .................. 10 2015 008 922

(51) Int. Cl.
| | |
|---|---|
| *A61B 3/10* | (2006.01) |
| *A61B 3/14* | (2006.01) |
| *A61B 3/02* | (2006.01) |
| *A61B 3/00* | (2006.01) |
| *A61B 3/103* | (2006.01) |

(52) U.S. Cl.
CPC ............ *A61B 3/103* (2013.01); *A61B 3/0025* (2013.01); *A61B 3/0033* (2013.01); *A61B 3/0075* (2013.01); *A61B 3/1035* (2013.01); *A61B 3/14* (2013.01)

(58) Field of Classification Search
CPC ........... A61B 3/135; A61B 3/103; A61B 3/14; A61B 3/113; A61B 3/1225; A61B 3/024; A61B 3/032; A61B 3/036; A61B 3/02; A61B 3/18; A61B 3/1015; A61B 3/12; A61B 3/117; A61F 9/008
USPC ............... 351/214, 200, 205, 206, 209, 210, 351/221–223, 239–246
See application file for complete search history.

(56) References Cited

U.S. PATENT DOCUMENTS

| | | |
|---|---|---|
| 6,550,917 B1 | 4/2003 | Neal et al. |
| 6,736,510 B1 | 5/2004 | Van Heugten |
| (Continued) | | |

FOREIGN PATENT DOCUMENTS

| | | |
|---|---|---|
| DE | 10 2008 047 400 A1 | 4/2010 |
| DE | 10 2010 024 606 A1 | 12/2011 |
| DE | 10 2014 116 152 A1 | 5/2016 |

OTHER PUBLICATIONS

Launay, G., "Optical Measuring Technology", BioPhotonik, 2009, pp. 38 and 39, and English translation thereof.
(Continued)

*Primary Examiner* — Dawayne Pinkney
(74) *Attorney, Agent, or Firm* — Walter Ottesen, P.A.

(57) ABSTRACT

An apparatus for determining ametropia of an eye includes an optical assembly with a light source, a detector, a plurality of optical elements and at least one stray light stop and a controller. An illumination beam path is provided between the light source and an optical interface in order to allow illumination light generated by the light source to emerge from the optical interface. A measurement beam path is provided between the optical interface and the detector in order to supply measurement light entering through the optical interface to the detector. The measurement beam path passes through an aperture of the at least one stray light stop. A diameter of this aperture is variable or a position of this aperture along the measurement beam path is variable in order to reduce stray light at the detector.

24 Claims, 5 Drawing Sheets

(56) References Cited

U.S. PATENT DOCUMENTS

| | | | |
|---|---|---|---|
| 8,459,795 B2 | 6/2013 | Seesselberg et al. | |
| 9,259,152 B2 | 2/2016 | Seesselberg et al. | |
| 2008/0165324 A1* | 7/2008 | Lindacher | A61B 3/028 351/159.41 |
| 2009/0213328 A1 | 8/2009 | Isobe et al. | |
| 2012/0268717 A1* | 10/2012 | Zhou | A61B 3/1015 351/221 |
| 2013/0076960 A1 | 3/2013 | Bublitz et al. | |
| 2014/0002795 A1 | 1/2014 | Yoshino | |
| 2014/0081247 A1 | 3/2014 | Heiberger et al. | |
| 2014/0139807 A1 | 5/2014 | Uchiyama | |
| 2015/0131053 A1* | 5/2015 | Copland | G02B 27/48 351/206 |
| 2017/0027437 A1* | 2/2017 | Neal | A61B 3/0025 |

OTHER PUBLICATIONS

Wesemann, W., "Functional principles and measurement precision of modern autorefractometers", DOZ Optometrie, 2004, pp. 38 to 44 and English translation thereof.

English translation and Office action of the German Patent Office dated Mar. 31, 2016 in German patent application 10 2015 008 922.6 on which the claim of priority is based.

* cited by examiner

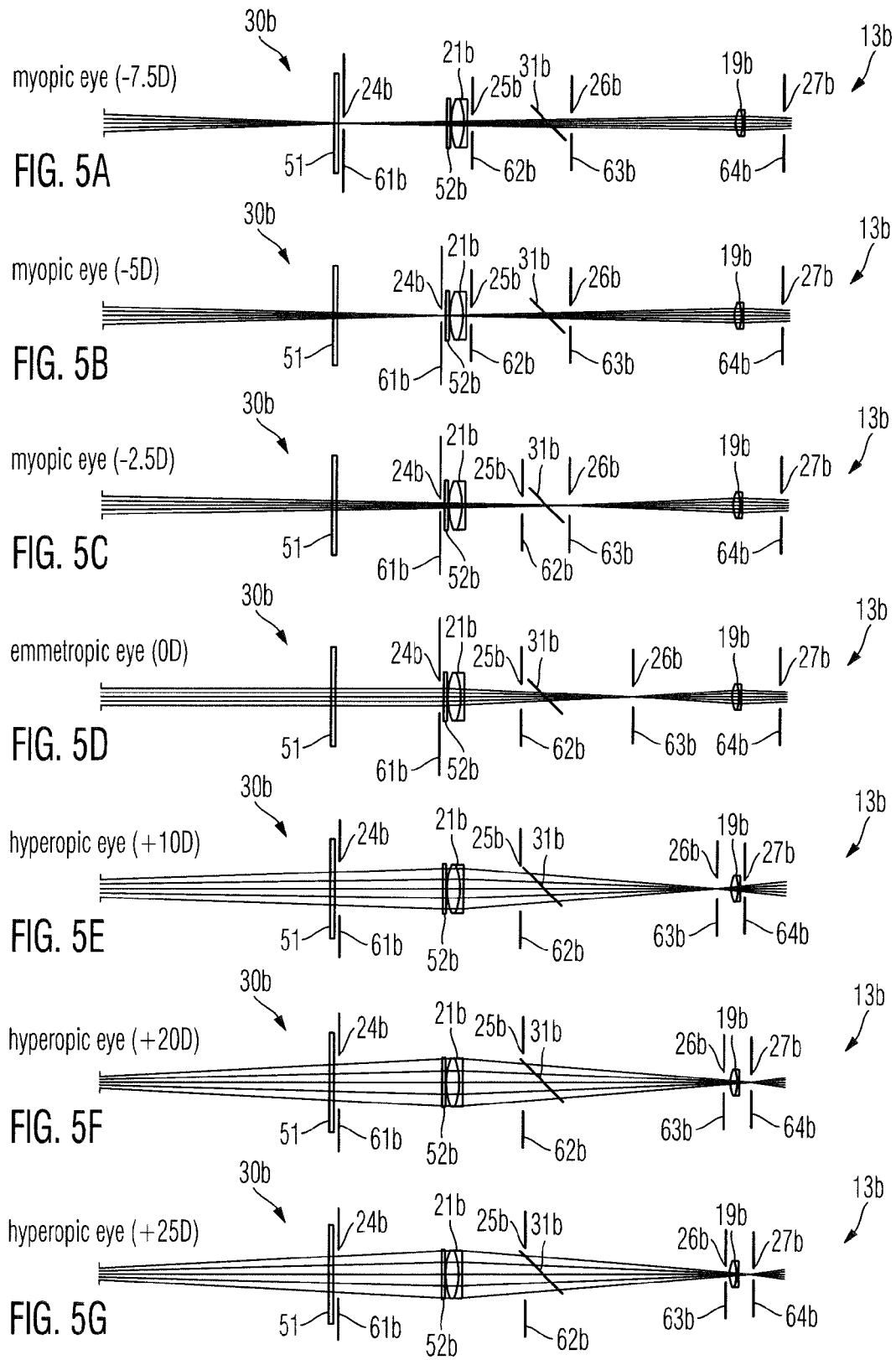

APPARATUS FOR DETERMINING AMETROPIA OF AN EYE

CROSS REFERENCE TO RELATED APPLICATION

This application claims priority of German patent application no. 10 2015 008 922.6, filed Jul. 10, 2015, the entire content of which is incorporated herein by reference.

FIELD OF THE INVENTION

The present invention relates to an apparatus for determining ametropia of an eye.

BACKGROUND OF THE INVENTION

An apparatus for determining the ametropia of an eye is suitable to determine the visual defect of an eye. By way of example, the determined visual defect of an eye of a patient can be the basis for a prescription of visual aids, such as, for example, spectacles or contact lenses, in order to correct the visual defect of the eye. The apparatus makes an optical measurement at the eye in order to determine the ametropia. Data which represent the ametropia of the measured eye are obtained by the optical measurement. These data typically represent a magnitude of a spherical visual defect and a magnitude and axis of an astigmatic visual defect of the eye. Furthermore, the determined ametropia of the eye can form the basis for planning a surgical intervention, such as, for example, a LASIK method, on the eye in order to improve the visual acuity thereof by changing the structure of the cornea with the aid of a laser beam. The optical measurement can be the apparatus directing an illumination light beam towards the eye in order to illuminate a small spot of the retina with light. Some of this light is scattered or reflected at the retina such that the small illuminated spot on the retina serves as a point light source for measurement light. This measurement light emerges from the eye as a light beam which is formed by the optical components of the eye, such as the vitreous humor, the lens and the curved cornea. This measurement light beam can be supplied to a detector for analysis purposes in order to deduce the optical properties of the optical components of the eye and hence the ametropia of the eye. By way of example, the detector can be a wavefront sensor, such as, for example, a Hartmann-Shack sensor. During the measurement using a wavefront sensor, it is possible to obtain data characterizing the ametropia of the eye, the data going beyond the magnitude of a spherical visual defect and the magnitude and axis of an astigmatic visual defect data usually used for the prescription of spectacles and enabling the correction of higher-order refractive errors, for example using the LASIK method.

In practice, it was found that it is not always simple to evaluate the detection signals obtained by the detector and to obtain therefrom data which represent the actual ametropia of the measured eye with high confidence.

SUMMARY OF THE INVENTION

Accordingly, it is an object of the invention to provide an apparatus for determining ametropia of an eye, which renders it possible to obtain data by way of measurements at an eye, the data representing ametropia of the measured eye with relatively high confidence.

In accordance with embodiments, an apparatus for determining ametropia of an eye includes an optical assembly and a controller. The optical assembly can include a light source, a detector, a plurality of optical elements and at least one stray light stop with an aperture. The optical assembly can be configured in such a way that an illumination beam path is provided between the light source and an optical interface in order to allow illumination light generated by the light source to emerge from the optical interface and that a measurement beam path is provided between the optical interface and the detector in order to supply measurement light entering through the optical interface to the detector. The measurement beam path can pass through the aperture of the at least one stray light stop, wherein a diameter of the aperture of the at least one stray light stop is variable. The apparatus can include a first actuator controlled by the controller in order to change the diameter of the aperture. Furthermore, a position of the aperture of the at least one stray light stop can be variable along the measurement beam path. Then, the apparatus can include a second actuator controlled by the controller in order to change the position of the aperture along the measurement beam path.

Within the meaning of the present application, optical elements are elements, via which the beam profile in the beam path can be influenced, that is, individual light rays can be deflected. Therefore, optical elements include, for example, lenses, which deflect light rays by light refraction, diffractive optical elements, which deflect light rays by light diffraction, and mirrors, which deflect light rays by light reflection.

In order to determine the ametropia of the eye using this apparatus, the eye is arranged relative to the optical interface of the apparatus in such a way that the illumination light emerging from the optical interface is able to enter into the eye and illuminate a spot on the retina of the eye. The light scattered and/or reflected at this illuminated spot on the retina emerges from the eye and enters into the optical assembly of the apparatus through the optical interface, the optical unit guiding the measurement light entering through the optical interface to the detector by way of the measurement beam path such that the detector can detect the measurement light. Then, using this, the controller can generate ametropia data on the basis of the detected measurement light, the ametropia data representing the ametropia of the eye. In particular, the ametropia data can represent a spherical visual defect and/or a magnitude and axis of an astigmatic visual defect of the eye.

By way of example, the detector can be a wavefront sensor, such as, for example, a Hartmann-Shack sensor. Other types of detectors are possible if the detection data thereof renders it possible to deduce the ametropia of the eye arranged at the optical interface.

The optical unit can include a beam splitter, through which the illumination beam path and the measurement beam path pass, wherein the illumination beam path and the measurement beam path are partly superposed on one another between the optical interface and the beam splitter.

In accordance with embodiments, at least a plurality of optical elements are passed by the illumination beam path and the measurement beam path. In accordance with further embodiments, at least one of the plurality of optical elements is passed through by the measurement beam path and not by the illumination beam path.

The apparatus includes one or more stray light stops, of which each one is adjustable in respect of the diameter of the aperture of the stray light stop and/or in respect of the position of the aperture along the measurement beam path.

This means that the at least one stray light stop may have a variable diameter which is changeable, for example, by an actuator which is controlled by the controller, while the position of the stray light stop along the measurement beam path is set and not changeable by an actuator which is controlled by the controller. Furthermore, the at least one stray light stop may have a set diameter which is not changeable by an actuator which is controlled by the controller, while the position of the stray light stop along the measurement beam path is variable and, for example, changeable by an actuator which is controlled by the controller. Furthermore, the at least one stray light stop may have both a variable diameter which is changeable, for example, by an actuator which is controlled by the controller and a variable position along the measurement beam path, wherein the position of the stray light stop along the measurement beam path is also changeable, for example, by an actuator which is controlled by the controller. The stray light stops serve to let light from the measurement beam path pass through the aperture such that it can reach the detector, while at least some of the stray light present in the optical assembly is absorbed by the stop such that it cannot reach the detector. In contrast to the light of the measurement beam path, which emanates from the retina of the eye to be measured and contains the information about the ametropia of the eye, the stray light does not contain such information and, if it reaches the detector, leads to the information contained in the light of the measurement beam path relating to the ametropia of the eye becoming more difficult to detect and evaluate.

The course of light rays in the measurement beam path and the size of the beam cross section of the measurement light emanating from the retina of the eye along the measurement beam path depends strongly on the ametropia of the eye to be measured. By way of example, the measurement light emanating from the retina of the eye is formed into a parallel measurement light beam by the eye in the case of an emmetropic eye, that is, an eye with normal vision, the measurement light beam entering into the optical assembly of the apparatus and being transformed by the optical elements of the optical assembly. In the case of a myopic eye, that is, an eye with near-sightedness, the measurement light emanating from the retina is formed into a convergent beam by the eye, the convergent beam likewise entering into the optical assembly and being transformed thereby. However, it is clear that the measurement light beams generated by a myopic eye have different beam cross sections at given positions along the measurement light beam path than the measurement light beam generated by the emmetropic eye.

The optical elements of the optical assembly, such as, for example, the lenses of the optical assembly, provide natural stops by the frames thereof, the stops delimiting the measurement light which can reach the detector. Due to the convergence or divergence of the measurement light beam entering into the optical assembly, which differs depending on the eye to be measured, it is possible that the frame of the optical element in the case of a given optical element of the optical assembly acts as a stop in the case of specific cases of ametropia of the eye by virtue of absorbing light from the measurement beam path or it does not act as a stop since the beam cross section of the measurement light beam at the position of the optical element is less than the effective optical cross section of the optical element itself.

The embodiment of the at least one stray light stop such that the diameter of the aperture thereof is adjustable renders it possible to set the diameter of the aperture at a given position of the stray light stop along the measurement beam path to such a size that substantially no measurement light is absorbed by the stray light stop and the measurement light reaches the detector with the greatest possible intensity, wherein the diameter of the aperture is set to be as small as possible in order to achieve this. Then, the stray light stop is effective in removing stray light from the beam path without adversely affecting the measurement light itself. Since the cross section of the measurement light beam at the given location of the stray light stop is different depending on the ametropia of the eye to be measured, the stray light stop can be adapted to the ametropia of the eye to be measured by changing the diameter of the aperture of the stray light stop, to be precise in such a way in each case that the diameter of the aperture is selected to be as small as possible in order to absorb as much stray light as possible and it is selected to be so large so as to allow as much measurement light as possible to pass through the aperture. In this way, it is possible to achieve an effective suppression of stray light reaching the detector for a multiplicity of types of ametropia of the eye to be measured.

In the case of a given diameter of the aperture, embodying the at least one stray light stop in such a way that the position of the aperture thereof is adjustable along the measurement beam path leads to the position of the stray light stop along the measurement beam path in the case of a given ametropia of the eye to be measured being adjustable in such a way that the beam cross section of the measurement light beam at the position of the aperture of the stray light stop has a diameter which is as large as, or only slightly smaller than, the diameter of the aperture of the stray light stop. Then, a large part of the measurement light can pass through the stray light stop towards the detector, while a part of stray light which is as large as possible is absorbed by the stray light stop so as not to reach the detector. Since the measurement light beam extends convergently or divergently within the optical assembly depending on the ametropia of the eye to be measured, it is possible to set a position in such a way that the condition explained above is satisfied by changing the position of the stray light stop along the measurement beam path.

The embodiment of the at least one stray light stop in such a way that both the diameter of the aperture thereof is adjustable and the position thereof along the measurement beam path is adjustable leads to it being possible to move the stray light stop to a position along the measurement beam path where the cross section of the measurement light beam has a particularly small diameter in the case of a given ametropia of the eye to be measured. If the stray light stop is arranged at such a position, the diameter of the aperture thereof can be reduced to such an extent that it substantially corresponds to the small diameter of the beam cross section at this position. Then, it is possible that a very large part of the stray light is absorbed by the stray light stop, while substantially the greatest possible component of the measurement light is able to pass through the aperture of the stray light stop towards the detector.

The range of positions along the measurement beam path, at which a given stray light stop can be arranged by changing the position thereof, may be restricted in certain cases. By way of example, components of the optical assembly arranged in a stationary manner provide such a restriction. By way of example, a stray light stop can be displaced between two optical elements, such as, for example, two lenses, which are arranged in the measurement beam path in a stationary manner. An effective suppression of stray light by way of this stray light stop alone is hardly possible if the diameter of the beam cross section of the measurement light beam is comparatively large everywhere in this region in the case of a specific ametropia of the eye to be measured. Therefore, two, three or more stray light stops are provided in some embodiments, the diameters of the apertures of which and/or the positions of the apertures of which along the measurement beam path are adjustable. In the specified case in which an effective suppression of stray light cannot be achieved with one stray light stop, which is selectively arrangeable at a position within a predetermined range along the measurement beam path, it is likely that another one of the further stray light stops can achieve an effective suppression of stray light.

The diameter of the aperture of the at least one stray light stop and/or the position of the aperture of the at least one stray light stop along the measurement beam path, which are to be set in order to achieve a substantial suppression of stray light at the detector, can be determined in different ways by the controller. In accordance with one embodiment, the controller is configured to establish a component of stray light in the light incident on the detector from the light intensity data provided by the detector and to actuate the first actuator and/or the second actuator on the basis of the established component of stray light. By way of example, the actuation can be carried out in such a way that the first actuator and/or the second actuator is tentatively actuated in a direction, in particular a randomly selected direction, and this direction of the actuation is maintained for as long as this results in a reduction in the component of stray light in the light incident on the detector. If a further reduction of the stray light incident on the detector then is no longer possible, a further actuator can be actuated in the same way in order to obtain, iteratively, a significant reduction of the stray light incident on the detector.

In accordance with further embodiments, the controller is configured to actuate the first actuator and/or the second actuator on the basis of ametropia data. The ametropia data represent measured or assumed ametropia of the eye to be measured. In particular, the ametropia data can represent a spherical visual defect and/or a magnitude and axis of an astigmatic visual defect of the eye to be measured. In accordance with embodiments, these ametropia data are established from light intensity data detected by the detector. In accordance with other embodiments, the ametropia data are fed to the controller from an external source by way of a data interface. By way of example, an estimated value for the ametropia of the eye to be measured can be known by the apparatus already prior to the measurement of the ametropia of the eye, and ametropia data, which represent this estimated value, can be used to set the diameter and/or the position along the measurement beam path of the aperture of the at least one stray light stop such that the measurement can already be started with effective suppression of stray light.

In accordance with embodiments, the device includes a memory or the controller is configured to access a memory via an interface, the memory containing settings data allowing the controller to determine an intended diameter and/or an intended position of the aperture of the at least one stray light stop on the basis of the settings data and the ametropia data and to actuate the first actuator and/or second actuator in such a way that the diameter of the aperture of the at least one stray light stop corresponds to the intended diameter and/or the position of the aperture of the at least one stray light stop along the measurement beam path corresponds to the intended position. By way of example, the settings data can include, in a table, values of intended diameters and intended positions depending on various values of the ametropia data. In accordance with other embodiments, the settings data include optical data of the optical assembly, which can be provided to a computer program which, for given ametropia data, is able to calculate the expected course of the measurement beam path and hence beam cross sections of the measurement light beam at various positions along the measurement beam path. Such a computer program is referred to as a ray tracing program. Examples for suitable ray tracing programs include CODE V by Synopsis, Mountain View, Calif., USA or ZEMAX by Radiant Visions Systems, Redmond, Wash., USA. It is then possible to establish suitable intended diameters and/or intended positions of the aperture of the at least one stray light stop which would suggest an effective suppression of stray light on the basis of the diameters of the beam cross section of the measurement light beam at different positions along the measurement light beam path, calculated by such a computer program.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
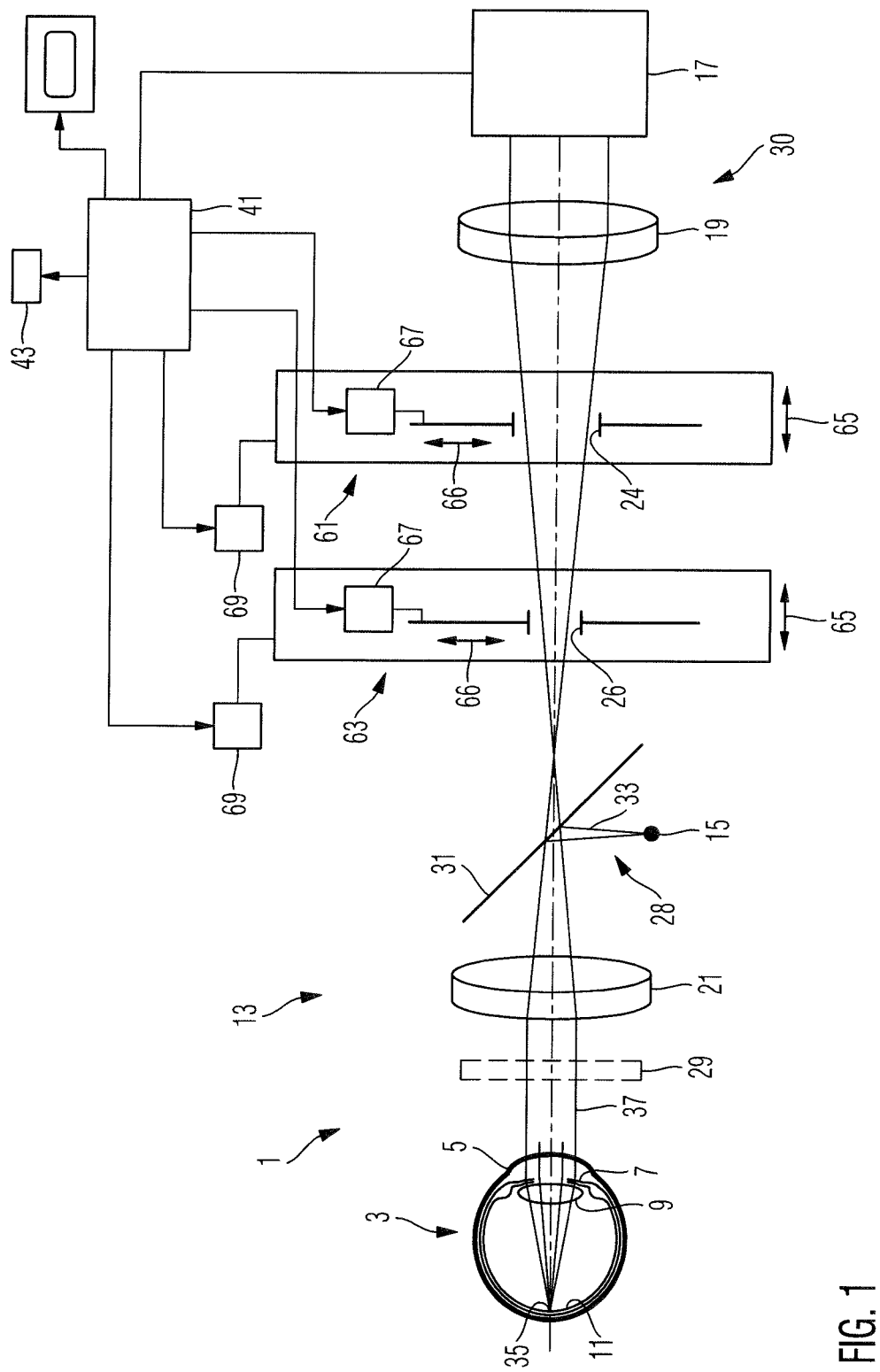
FIG. 1 is a schematic of an apparatus for determining ametropia of an eye in accordance with one embodiment.

FIG. 1 is a schematic of an apparatus 1 for determining ametropia of an eye 3. The eye 3 includes a cornea 5, an iris 7, a natural lens 9 and a retina 11. The apparatus 1 includes an optical assembly 13, which includes a light source 15, a detector 17, a plurality of lenses 19 and 21, and two stray light stops 61 and 63. The optical assembly 13 provides an illumination beam path 28 between the light source 15 and the eye 3, and a measurement beam path 30 between the eye 3 and the detector 17. The eye 3 is not part of the apparatus and can, for example, be removed from the beam paths or be replaced by another eye. However, the optical assembly has an optical interface 29, which is passed through by the illumination beam path 28 and the measurement beam path 30. In order to undertake a measurement on an eye 3, the latter must be positioned relative to the optical interface 29 in such a way that the eye 3 becomes part of the illumination beam path 28 and the measurement beam path 30.

The lenses 19 and 21 are only examples of optical elements which influence the beam profile and deflect individual light rays of a beam. Other examples of optical elements are diffractive optical elements and mirrors, which can be used in the optical assembly 13 in place of the lenses or in addition to the lenses. The optical assembly 13 with the two lenses 19 and 21 is likewise exemplary within the sense of it being possible for a larger number of optical elements to be used in other embodiments. Furthermore, in the depicted example, one lens is passed through by both the illumination beam path and the measurement beam path while another lens is only passed through by the measurement beam path. In other embodiments, it can also be possible that optical elements which are passed through by both the illumination beam path and the measurement beam path are not provided. By way of example, this is possible if the illumination beam path and the measurement beam path pass through the optical interface next to one another and not in an overlapping form or if no optical elements are arranged in the beam path between the beam splitter and the eye. Then the eye, and in particular the cornea thereof, forms the only source of stray light.

The illumination beam path 28 extends between the light source 15 and the optical interface 29 and contains a beam splitter 31 and the lens 21. Light emitted by the light source 15 forms an illumination light beam 33, which is reflected at the beam splitter 31, passes through the lens 21 and emerges from the optical assembly 13, and hence from the apparatus 1, by way of the optical interface 29. If the eye 3 is positioned correctly relative to the optical interface 29, the illumination light beam 33 passes through the cornea 5 and the lens 9 of the eye 3 and illuminates a small spot 35 on the retina 11. Some of the illumination light is scattered or reflected at the retina 11 of the eye 3, and so, proceeding from the spot 35, it passes through the natural lens 9 and the iris 7 and emerges from the eye via the cornea 5 and forms a measurement light beam 37 in the process, the measurement light beam entering the optical assembly 13 via the optical interface 29. There, the measurement light beam 37 passes through the lens 21, the beam splitter 31, an aperture 26 of the stray light stop 63, an aperture 24 of the stray light stop 61 and the lens 19 along the measurement beam path 30 in order finally to enter into the detector 17. The detector 17 detects light intensities of the measurement light beam 37 and generates light intensity data corresponding to the light intensities. The light intensity data are transferred from the detector 17 to a controller 41, which evaluates the light intensity data. This evaluation contains determining ametropia data representing the ametropia of the eye 3. By way of example, by way of the controller 41, the ametropia data can be output by way of a data interface 43 or depicted on a monitor 45.

Since the measurement light beam 37 was generated by the optical components of the eye 3, the measurement light beam 37 contains information about the ametropia of the eye 3. The detector 17 is suitable to detect light intensities of the measurement light beam in such a way that the ametropia data, which represent the ametropia of the eye 3, can be established by the controller 41 from the obtained intensity data. To this end, the detector can include a wavefront sensor, such as, for example, a Hartmann-Shack sensor. To this end, the detector 17 can likewise include a type of sensor as described in U.S. Pat. 9,259,152. Furthermore, the detector can include a type of sensor which is denoted a Talbot-Moiré sensor and which is described in, for example, U.S. Pat. 6,736,510 B1. Furthermore, the detector can include a type of sensor which is embodied as a digital wavefront aberrometer, as described in the article "Digitale Wellenfrontmessungen in der ophthalmologischen Aberrometrie" [Digital wavefront measurements in ophthalmic aberrometry], BioPhotonik 2009 by Gael Launay. Other types of sensors are also conceivable for realizing the detector 17.

The optical assembly 13 explained on the basis of FIG. 1 includes two lenses 19 and 21, wherein the lens 21 is passed by both the illumination beam path 25 and the measurement beam path 27 while the lens 19 is only passed by the measurement beam path 27. However, it is possible that, additionally, further lenses are arranged in the measurement beam path 27 and/or in the illumination beam path 25. In particular, the detector 17 can also include one or more lenses, through which the measurement light beam 37 passes. Furthermore, each lens of the optical assembly 13 can include one or more lens elements. In the illustration of FIG. 1, each lens 19 and 21 is depicted as a lens which includes two cemented lens elements. A greater number of cemented lens elements per lens is possible. The lenses 19 and 21 and the detector 17 of the optical assembly 13 explained on the basis of FIG. 1 are arranged in a stationary manner relative to the remaining components of the optical unit 13. However, it is possible that one or more of the lenses or components of the detector are displaceable along the measurement beam path in order to adapt the optical assembly to certain circumstances, such as, for example, the actual ametropia of the measured eye.

In the optical assembly 13 schematically depicted in FIG. 1, the illumination light beam 33 is reflected at the beam splitter 31 while the measurement light beam 37 passes through the beam splitter. However, it is also possible to embody the optical assembly 13 in such a way that the illumination light beam 33 passes through a beam splitter while the measurement light beam 37 is reflected at the beam splitter. By making use of the beam splitter 31, the illumination beam path 28 and the measurement beam path 30 are superposed on one another in the region between the optical interface 29 and the beam splitter 31 in such a way that these emerge from, or enter into, the optical interface 29 in a superposed manner. However, it is likewise possible to obtain a similar superposition not physically by a beam splitter but only geometrically by way of a small mirror, at which the illumination light beam 33 is reflected. Furthermore, it is possible that the illumination light beam 33 and the measurement light beam 37 pass through the optical interface 29 next to one another and substantially not overlapping one another.

The light source 15 can be formed by any suitable light source and, for example, include a light-emitting diode, an incandescent light or a laser. It can also be formed by an exit end of a light guide, into which light is fed at the end lying opposite to the exit end. The light source 15 can furthermore include one or more lenses or other optical elements in order to form the illumination light beam 33.

Figure 2:
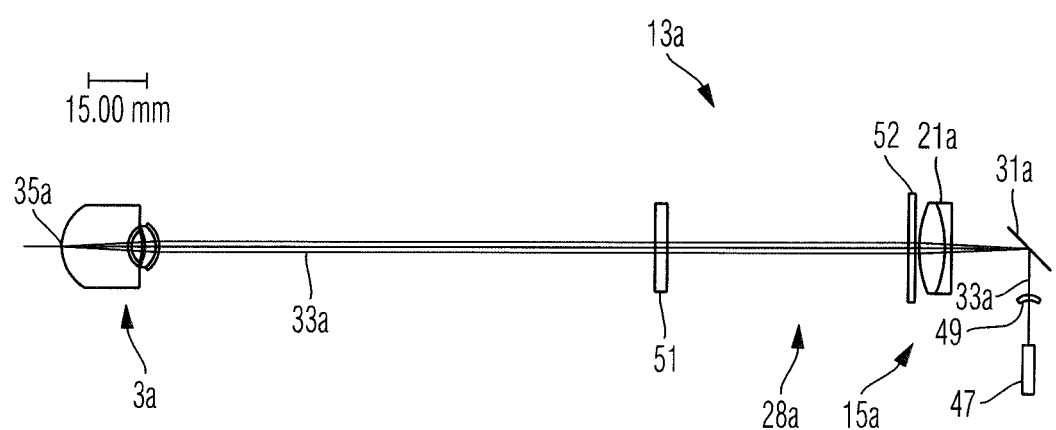
FIG. 2 is a detailed illustration for explaining an illumination beam path of an apparatus, similar to the one in FIG. 1, for determining ametropia of an eye in accordance with a further embodiment.

FIG. 2 is a schematic illustration of part of an optical assembly 13a of an embodiment of an apparatus for determining ametropia of an eye 3a, which is similar to the apparatus in FIG. 1. FIG. 2 serves to explain an illumination beam path 28a. A light source 15a includes one end of a light guide 47, from which an illumination light beam 33a emerges and passes through a stop 49 with an aperture which defines the cross section of the illumination light beam 33a. The illumination light beam 33a is reflected at a beam splitter 31a, passes through a lens 21a and a thin quartz window 52 and emerges from the optical assembly 13a via a window 51 towards the eye 3a. The illumination light beam 33a passes through the optical components of the eye 3a and illuminates a spot 35a on the retina 11a thereof. By way of example, the thin quartz window 52 can be a $\lambda/4$ plate. This is advantageous if the beam splitter 31a is embodied as a polarizing beam splitter and if the orientation of the $\lambda/4$ plate is matched to the polarizing beam splitter. Then, the component of the light reflected at the spot 35a on the retina 11a and reaching the detector can be increased relative to the stray light. However, the thin quartz window 52 can also have no polarizing properties and partly transmit and reflect light.

On its way to the retina 11a of the eye 3a, the light of the illumination light beam 33a passes through various optically effective boundary surfaces and is partly reflected or scattered thereon. This reflected or scattered light of the illumination light beam 33a is, once again, at least partly superposed on a measurement beam path of the optical assembly 13a and can reach the detector without containing information about the ametropia of the eye to be measured. This light interfering with the detection of the measurement light of interest is generally referred to as scattered light, even if it arises as a result of a reflection on optical components.

FIGS. 3A to 3D are detailed illustrations of the optical assembly 13a in FIG. 2 and serve to explain causes of stray light in the optical assembly 13a. Here, exemplary rays of stray light are respectively depicted in each one of FIGS. 3A to 3D, which rays arise by reflection at a single optical boundary surface. Only those rays of stray light which can ultimately reach the detector of the optical assembly 13a (not depicted here) are depicted. Furthermore, the rays of the illumination light beam 33a are only depicted in part, to be precise, when proceeding from the stop 49, only as far as the optical boundary surface, the stray light of which is depicted in the respective figure.

Figure 3A:
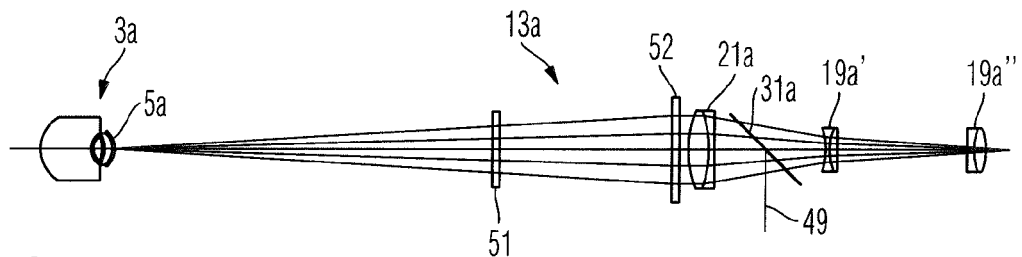
FIGS. 3A to 3D are detailed illustrations of the apparatus in FIG. 2 for explaining arising stray light.

FIG. 3A shows stray light which arises as a result of reflection of the illumination light at the cornea of the eye 3. Due to the difference in the refractive indices of air and cornea, the surface of the cornea forms an optical boundary surface at which the illumination light is reflected. Typically, 2% to 4% of the illumination light incident on the cornea is reflected by the latter and some of this light can, as depicted in FIG. 3A, reach the detector as interfering stray light.

Figure 3B:
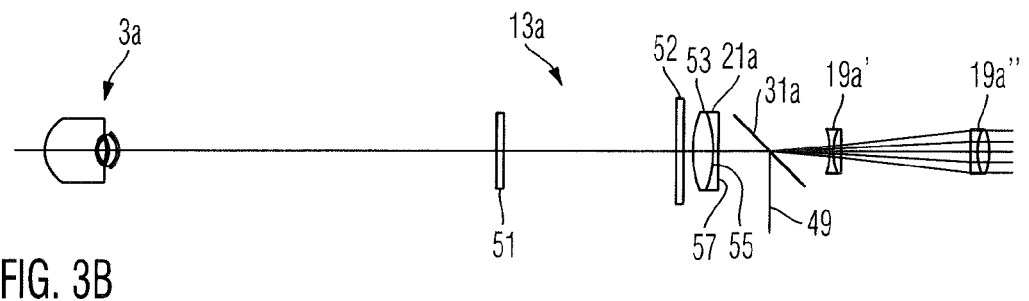

FIG. 3B shows stray light which arises as a result of reflection of the illumination light at a surface 53 of the lens 21a and which can reach the detector. Even if the surface 53 of the lens 21a has an antiglare property, for example as a result of applying suitable dielectric layers, for example, 0.1% to 1% of the illumination light passing through the surface 53 of the lens 21a is nevertheless reflected at this surface and forms stray light which interferes with the measurement.

Figure 3C:
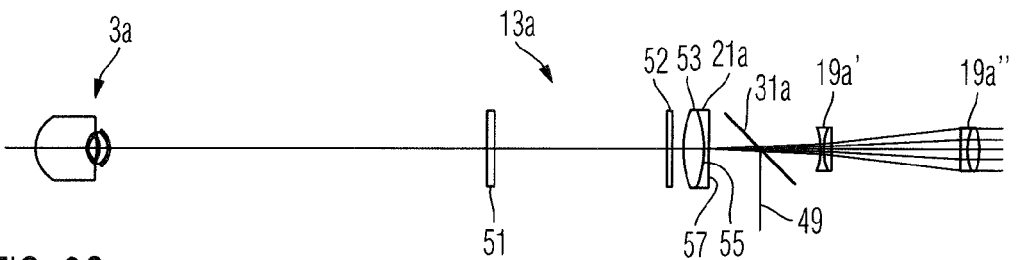

FIG. 3C shows stray light which is generated by illumination light which is generated at an inner boundary surface 55 between two lens elements 56 and 57 of the lens 21a and which can reach the detector. Typically, 0.1% to 1% of the illumination light passing through the boundary surface 55 is reflected at this boundary surface.

Figure 3D:
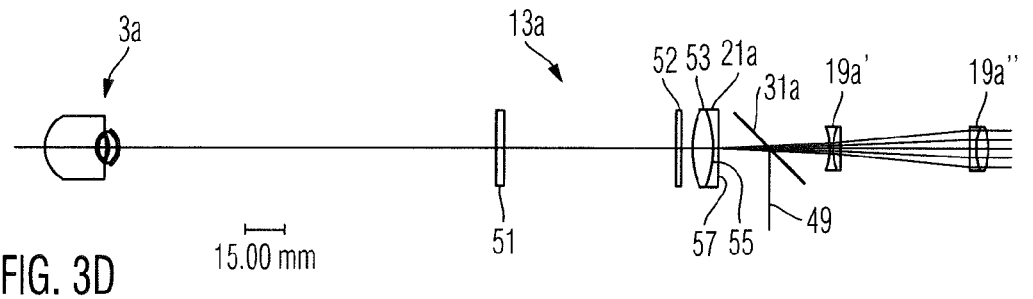

FIG. 3D shows stray light which is generated by illumination light which is reflected at a surface 57 of the lens 21a and which can reach the detector. Even in the case of an antiglare surface 57, for example, 0.1% to 1% of the illumination light can be reflected at this surface.

Figure 4A:
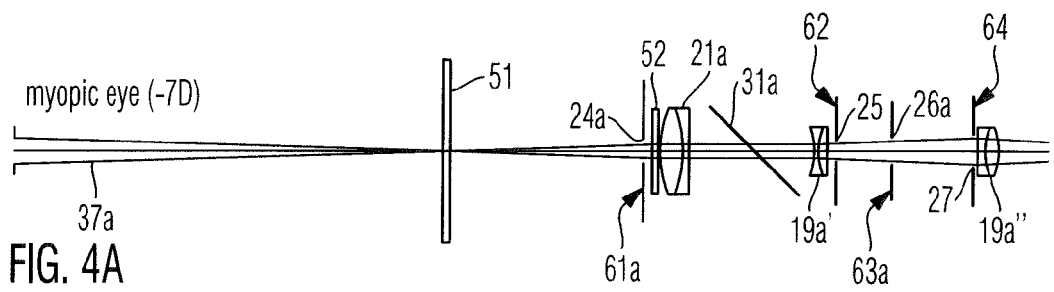
FIGS. 4A to 4E are detailed illustrations of the apparatus in FIGS. 2 and 3 for explaining stray light stops in a measurement beam path; and, FIGS. 5A to 5G are detailed illustrations for explaining stray light stops in a measurement beam path of an apparatus, similar to the apparatuses in FIGS. 1 to 4E, for determining ametropia of an eye in accordance with a further embodiment.
Figure 4B:
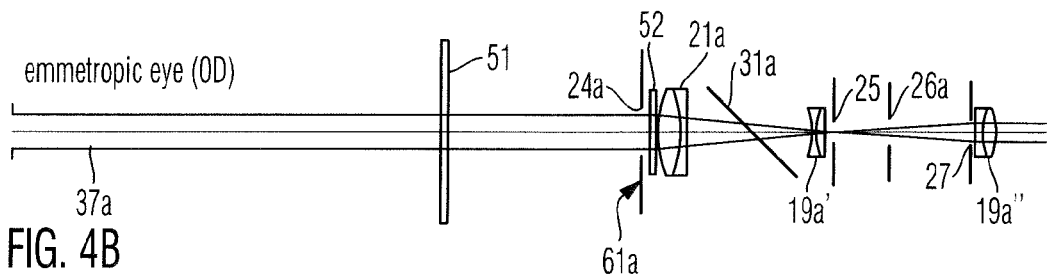
Figure 4C:
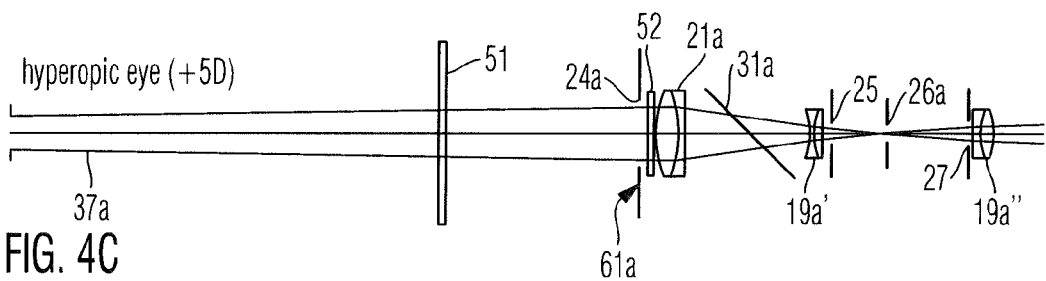
Figure 4D:
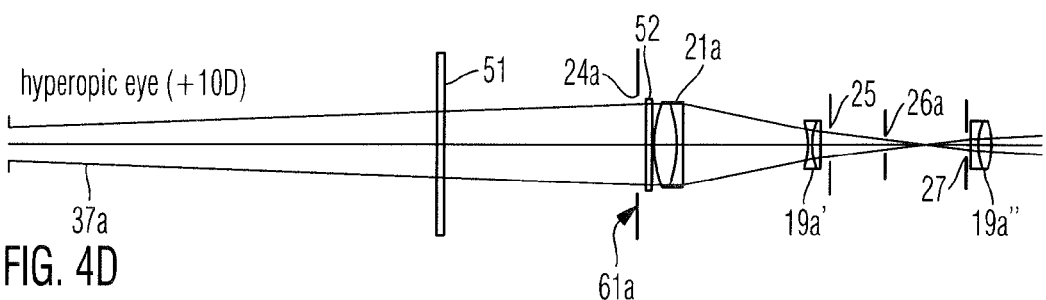
Figure 4E:
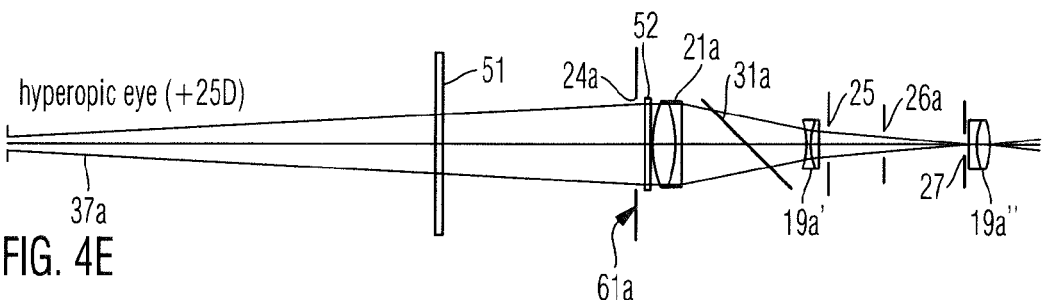

FIGS. 4A to 4E serve to explain the measurement beam path of the embodiment, explained in FIGS. 2 and 3, of an apparatus for determining ametropia of an eye 3a. Once again, FIGS. 4A to 4E depict in an exemplary manner only those rays which also reach the detector (not depicted here). Depending on ametropia of the measured eye, the measurement light emerges from the eye with differing convergences and enters the optical assembly 13a. FIGS. 4A to 4E differ in respect of the ametropia of the measured eye. FIG. 4A shows the measurement light beam for a myopic eye with −7D, FIG. 4B shows the measurement light beam for an emmetropic eye (OD), FIG. 4C shows the measurement beam path for a hyperopic eye with +5D, FIG. 4D shows the measurement beam path for a hyperopic eye with +10D and FIG. 4E shows the measurement beam path for a hyperopic eye with +25D. In each one of FIGS. 4A to 4E, the measurement light beam 37a passes through the entrance window 51, the lens 21a, the beam splitter 31a and two lenses 19a' and 19a", before the measurement light is detected.

By comparing FIGS. 4A to 4E, it is possible to identify that the cross section of the measurement light beam 37a at given positions along the measurement beam path is very different depending on the ametropia of the measured eye. By way of example, the diameter of the beam cross section of the measurement light beam 37a directly upstream of the lens 21a is relatively small for the myopic eye, while it is relatively large at this position for hyperopic eyes. Furthermore, a crossover with a particularly small beam cross section is formed between the lenses 19a' and 19a" for emmetropic and hyperopic eyes, while this is not the case for the myopic eye.

Below, reference is made to FIG. 1 in order to explain the realization of stray light stops in the measurement beam path 27. The depicted optical assembly 13 has a first stop arrangement 61 and a second stop arrangement 63. Each one of the stop arrangements includes a holder, which holds a light-absorbing plate-shaped structure relative to the measurement beam path 27 in such a way that the aperture 24 in the plate-shaped light-absorbing structure of the stop arrangement 61 and the aperture 26 in the plate-shaped light-absorbing structure of the stop arrangement 63 are sufficiently centered in relation to the measurement beam path 27 such that the measurement light beam 37 can pass through the apertures 24 and 26, while stray light is largely caught by the plate-like light-absorbing structures.

Each one of the stop arrangements 61 and 63 is arranged in a manner displaceable in the direction of the measurement beam path, as indicated by the double-headed arrows 65 in FIG. 1. The apparatus 1 furthermore includes an actuator 69 for each stop arrangement (61, 63), the actuator being controlled by the controller 41 in order to set the position of the respective stop arrangement (61, 63) and, in particular, the position of the aperture (24, 26) of the stop arrangement (61, 63) in the direction of the measurement beam path 27.

Furthermore, a diameter of the aperture (24, 26) in the plate-shaped light-absorbing structures of the stop arrangements 61 and 63 is adjustable, as represented in FIG. 1 by double-headed arrows 66. For each stop arrangement (61, 63), the apparatus 1 includes an actuator 67, which is controlled by the controller 41 in order to adjust the diameter of the respective aperture 24 or 26. By way of example, the stop arrangements (61, 63) can include iris diaphragms, which have a multiplicity of sickle-shaped elements arranged around a center in the circumferential direction, the elements forming the plate-like light-absorbing structure and defining the aperture (24, 26). The sickle-shaped elements are displaceable by the actuator 67 in order to adjust the diameter of the aperture.

The stop arrangements 61 and 63 explained on the basis of FIG. 1 each have an aperture 24, 26, the position of which along the measurement beam path 27 is adjustable and the diameter of the aperture (24, 26) of which is adjustable. Hence, these stop arrangement 61 and 63 provide two functionalities, namely, firstly, the position along the measurement beam path 27, which is adjustable by the actuator 69, and, secondly, the diameter of the aperture (24, 26), which is adjustable by the actuator 67. However, it is also possible for one or more of the stray light stops to only provide one of these two functionalities. Therefore, one or more of the stray light stops can have a position along the measurement beam path which is adjustable by way of an actuator 69, while the diameter of the aperture is not changeable, or the diameter of the aperture of the stray light stop can be changeable, while the position thereof along the measurement beam path is not changeable.

The suppression of stray light with the aid of stray light stops is explained below on the basis of FIGS. 4A to 4E. The optical assembly 13a of the embodiment of the apparatus 1a, depicted in FIGS. 2 to 4, for determining ametropia of an eye includes four stray light stop arrangements 61a, 62, 63a and 64, which each have a plate-shaped light-absorbing structure with an aperture 24a, 25, 26a and 27. The diameters of the apertures 24a, 25, 26a and 27 are each adjustable by an actuator not depicted in FIGS. 4A to 4E, the actuators being controlled by a controller of the apparatus 1a. However, the positions of the apertures 24a, 25, 26a and 27 along the measurement beam path are fixed. The diameters of the apertures 24a, 25, 26a and 27 are respectively set by the controller in a manner dependent on the measured ametropia of the eye in such a way that the rays of the measurement light, emanating from the eye and reaching the detector, can all pass through the apertures 24a, 25, 26a and 27, wherein each one of the diameters of the apertures is selected to be as small as possible in order to achieve this goal. Then, a portion of the stray light which is as large as possible is absorbed by the plate-shaped light-absorbing structures and can therefore not reach the detector. From a comparison between FIGS. 3A and 4A, it is possible to identify that the stop arrangement 61a is particularly effective at absorbing stray light generated by reflection at the cornea in the case of a myopic eye. By comparing FIGS. 3A and 4E, it is clear that this stop arrangement 61a cannot substantially reduce the stray light reflected at the cornea in the case of a hyperopic eye since the aperture 24a of the stop arrangement 61a in the case of a hyperopic eye should be set to a large diameter in order to let the whole measurement light pass in the direction of the detector. However, the diameter of the aperture 27 of the stop arrangement 64 can be set to be particularly small in the case of the hyperopic eye (cf. FIG. 4E) in order to absorb as much stray light as possible and, at the same time, let the whole measurement light pass through since the measurement beam path for the hyperopic eye has a crossover in the vicinity of the position of the aperture 27 of the stop arrangement 64. Such a crossover is also formed in the case of the emmetropic eye between the lenses 19a' and 19a" (cf. FIG. 4B). Depending on the strength of the hyperopia, the crossover is formed at different positions between the lens 19a' and the lens 19a". By using three apertures 25, 26a and 27 of the stop structures 62, 63a and 64, the diameter of which is adjustable in each case, it is however possible to be able to set at least the diameter of one of the apertures 25, 26a and 27 to be very small for each value of the hyperopia in order to absorb a component of the stray light which is as large as possible.

The diameters of the apertures 24a, 25, 26a and 27 can be set by the controller in a manner dependent on the measured ametropia of the currently measured eye. To this end, the controller can include a memory or have access to a memory, in which the diameters of the apertures of the stray light stops, which lead to the best possible suppression of stray light, are stored for a multiplicity of values of ametropia. These ideal diameters of the apertures could have been determined in advance by calculation or experiment. However, it is also possible for the controller to carry out a computational program which calculates beam profiles of the measurement light beam through the optical assembly in a manner dependent on the measured ametropia of the measured eye. The controller can then set the diameters of the apertures 24a, 25, 26a and 27 in accordance with the calculated diameters of the beam cross section of the measurement light beam at the positions of the respective stray light stops.

The optical data of the optical assembly 13a explained on the basis of FIGS. 2 to 4 are specified in the subsequent Table 1. Here, in the first column, the optical faces used in an optical computational program are numbered from S1 to S26. The second column specifies the radius of curvature in millimeters; the center of the curvature lies to the left of the face in the illustration of the figures in the case of a negative value and it lies to the right thereof in the case of a positive value. "INF" describes a plane face with an infinite radius of curvature. The third column specifies the distance of the face from the subsequent face along the optical axis in mm. The fourth column specifies the optically effective material which is provided at the face and the subsequent face. The references correspond to the glass catalogue by Schott, Germany, with an empty entry denoting air. The fifth column specifies half the optically effective diameter of the face in the beam path. The faces S8 to S10 describe the lens 21a, the faces S15 to S17 describe the lens 19a', the faces S21 to S23 describe the lens 19a", the face S11 describes the beam splitter 31a, which is assumed to be thin, the face S5 describes the stray light stop 24a, the face S18 describes the stray light stop 25, the face S19 describes the stray light stop 26a, the face S20 describes the stray light stop 27, S13 and S14 denote auxiliary faces, on which further stray light stops may also be arranged.

TABLE 1

| Face: | Radius of curvature [mm] | Thickness [mm] | Glass | Radius [mm] |
|---|---|---|---|---|
| S1 | --- Stop --- | 128.750000 | | 4.000 |
| S2 | INF | 2.000000 | NBK7 | 26.500 |
| S3 | INF | 29.900000 | | 26.500 |
| S4 | INF | 30.000000 | | |
| S5 | INF | 3.500000 | | |
| S6 | INF | 1.100000 | Quartz | 12.600 |
| S7 | INF | 1.000000 | | 12.600 |
| S8 | 33.018000 | 5.800000 | N-BAF10 | 11.200 |
| S9 | −28.184000 | 1.700000 | N-SF6 | 11.200 |
| S10 | −177.830000 | 19.436025 | | 11.200 |
| S11 | INF | 0.000000 | NBK7 | 17.819 |
| S12 | INF | 9.430000 | | 17.819 |
| S13 | INF | 7.000000 | | |
| S14 | INF | 3.000000 | | |
| S15 | −23.207000 | 1.000000 | N-SSK8 | 6.250 |
| S16 | 19.953000 | 2.200000 | N-SF56 | 6.200 |
| S17 | 77.741000 | 1.000000 | | 6.200 |
| S18 | INF | 18.000000 | | |
| S19 | INF | 24.167474 | | |
| S20 | INF | 1.000000 | | |
| S21 | 49.403000 | 2.300000 | N-SF5 | 6.250 |
| S22 | 17.783000 | 4.000000 | N-BK7 | 6.200 |
| S23 | −25.119000 | 1.000000 | | 6.200 |
| S24 | INF | 13.000000 | | |
| S25 | INF | 1.000000 | | |
| S26 | INF | 0.000000 | | |

FIGS. 5A to 5G are detailed illustrations of an optical assembly 13b of an apparatus 1b, similar to the apparatuses of FIGS. 1 to 4, for determining ametropia of an eye. FIGS. 5A to 5G serve to explain a measurement beam path 30b of the device 1b, with, once again, only those rays which reach the detector (not depicted here) being depicted in an exemplary manner.

Arranged in the measurement beam path 27b are four stray light stops, the apertures 24b, 25b, 26b and 27b of which are adjustable in respect of the diameter thereof and in respect of the position thereof along the beam path 27b by way of actuators. In particular, the position of the aperture 24b along the measurement beam path 27b can be set in a range between an entrance window 51b and a lens 21b. The position of the aperture 25b can be set in a range of the measurement beam path 27b between the lens 21b and a beam splitter 31b. The position of the aperture 26b can be set in a range of the measurement beam path 27b between the beam splitter 31b and a lens 19b. The position of the aperture 27b can be set along the measurement beam path 27b in a range between the lens 19b and a detector (not depicted in FIGS. 5A to 5G).

FIGS. 5A to 5G differ in respect of the ametropia of the measured eye. For any entropy of the measured eye, each one of the apertures of the stray light stops is moved along the measurement beam path 27b in the range available to the stray light stop to such a position at which the diameter of the beam cross section of the measurement light beam 37b is smallest. There, the diameter of the aperture is set to be as small as possible in order to absorb as much stray light as possible, but in order to absorb no light of the measurement light beam.

The optical data of the optical assembly 135 explained on the basis of FIGS. 5A to 5G are specified in the subsequent Table 2. Here, in the first column, the optical faces used in an optical computational program are numbered from S1 to S18 and the further columns provide the same specifications as the corresponding columns in Table 1 described above. The faces S7 to S9 describe the lens 21b, the faces S14 to S16 describe the lens 19b, the face S10 describes the beam splitter 31b, which is assumed to be thin. The remaining faces denote auxiliary faces. The stray light stops 24b, 25b, 26b and 27b are displaceable along the optical axis and therefore do not have a fixed position and are correspondingly not specified in Table 2

TABLE 2

| Face | Radius of curvature [mm] | Thickness [mm] | Glass | Radius [mm] |
|---|---|---|---|---|
| S1 | INF | 128.750000 | | 4.000 |
| S2 | INF | 2.000000 | NBK7 | 26.500 |
| S3 | INF | 29.900000 | | 26.500 |
| S4 | INF | 33.500000 | | |
| S5 | INF | 1.100000 | Quartz | 12.600 |
| S6 | INF | 1.000000 | | 12.600 |
| S7 | 61.748000 | 6.250000 | N-BK7 | 12.700 |
| S8 | −44.348000 | 2.750000 | N-SF5 | 12.700 |
| S9 | −128.640000 | 48.114448 | | 12.700 |
| S10 | INF | 0.000000 | NBK7 | |
| S11 | INF | 48.114448 | | |
| S12 | INF | 0.000000 | | |
| S13 | INF | 57.884050 | | |
| S14 | 74.989000 | 2.300000 | N-SF5 | 6.250 |
| S15 | 26.322000 | 3.000000 | N-BK7 | 6.200 |
| S16 | −37.449000 | 24.537375 | | 6.200 |
| S17 | INF | 0.000000 | | |
| S18 | INF | | | |

The apparatus for determining ametropia of an eye, described above, can be complemented in order to be able to carry out further functions. By way of example, the apparatus for determining ametropia of an eye can be integrated with a surgical microscope, as shown in, for example, FIG. 9 of DE 10 2010 024 606 A1 for a conventional apparatus for determining ametropia of an eye. Furthermore, the apparatus for determining ametropia of an eye can be integrated with a display module for optical visualization, wherein a user controls functions of the display module by accommodating his eye. An example of such display module is described in United States patent application publication 2013/0076960, wherein the display module in that case has a conventional apparatus for determining ametropia of an eye.

It is understood that the foregoing description is that of the preferred embodiments of the invention and that various changes and modifications may be made thereto without departing from the spirit and scope of the invention as defined in the appended claims.

What is claimed is:

1. An apparatus for determining ametropia of an eye, the apparatus comprising:
    an optical assembly including a light source, a detector, a plurality of optical elements and a first stray light stop having an aperture;
    said light source being configured to generate illumination light;
    an optical interface;
    a controller;
    said optical assembly being configured such that an illumination beam path is provided between said light source and said optical interface in order to allow said illumination light generated by said light source to emerge from said optical interface;
    said optical assembly being further configured such that a measurement beam path is provided between said optical interface and said detector in order to supply measurement light entering through said optical interface to said detector;
    said measurement beam path passing through said aperture of said first stray light stop;
    said aperture of said first stray light stop having a variable diameter;
    a first actuator;
    said controller being configured to control said first actuator so as to change the diameter of the aperture;
    said optical assembly further including a second stray light stop having a second aperture, wherein said measurement beam path passes through said second aperture of said second stray light stop;
    said second aperture of said second stray light stop having at least one of a variable diameter and a variable position along said measurement beam path;
    a second actuator; and,
    said controller being configured to control said second actuator so as to change at least one of the diameter of the second aperture and the position of the second aperture along said measurement beam path.

2. The apparatus of claim 1, wherein:
    said aperture has a variable position along said measurement beam path; and,
    said controller is configured to control said second actuator so as to change said position of said aperture along said measurement beam path.

3. The apparatus of claim 1, wherein:
    said controller is configured to set said diameter of said first aperture such that at least a portion of the light of said light source which is reflected or scattered into the measurement beam path at optical boundary surfaces in said illumination beam path is absorbed by said first stray light stop.

4. The apparatus of claim 2, wherein said controller is configured to set at least one of:

said diameter of said aperture such that at least a portion of the light of said light source which is reflected or scattered into the measurement beam path at optical boundary surfaces in said illumination beam path is absorbed by said stray light stop; and, said position of said aperture being such that at least a portion of the light of said light source which is reflected or scattered into the measurement beam path at optical boundary surfaces in said illumination beam path is absorbed by said stray light stop.

5. The apparatus of claim 3, wherein in the case of at least one ametropia of the eye, an intensity of the component of light absorbed by said first stray light stop is one of at least 0.3-times, at least 0.6-times and at least 0.9-times the total intensity of the light incident on said detector when said first stray light stop is removed from said measurement beam path.

6. The apparatus of claim 4, wherein in the case of at least one ametropia of the eye, an intensity of the component of light absorbed by said first stray light stop is one of at least 0.3-times, at least 0.6-times and at least 0.9-times the total intensity of the light incident on said detector when said first stray light stop is removed from said measurement beam path.

7. The apparatus of claim 1, wherein:
said detector is configured to detect light intensity and provide light intensity data; and,
said controller is configured to obtain said light intensity data from said detector and to establish ametropia data representing the ametropia of the eye from said light intensity data.

8. The apparatus of claim 2, wherein:
said detector is configured to detect light intensity and provide light intensity data; and,
said controller is configured to obtain said light intensity data from said detector and to establish ametropia data representing the ametropia of the eye from said light intensity data.

9. The apparatus of claim 1 further comprising:
a data interface; and,
said controller being configured to obtain ametropia data representing the ametropia of the eye via said data interface.

10. The apparatus of claim 8, wherein said ametropia data represent at least one of:
a spherical visual defect; and,
a magnitude and axis of an astigmatic visual defect of the eye.

11. The apparatus of claim 9, wherein said ametropia data represent at least one of:
a spherical visual defect; and,
a magnitude and axis of an astigmatic visual defect of the eye.

12. The apparatus of claim 8, wherein said controller is configured to actuate at least one of said first actuator and said second actuator on the basis of said ametropia data.

13. An apparatus for determining ametropia of an eye, the apparatus comprising:
an optical assembly including a light source, a detector, a plurality of optical elements and at least one stray light stop having an aperture;
said light source being configured to generate illumination light;
an optical interface;
a controller;
said optical assembly being configured such that an illumination beam path is provided between said light source and said optical interface in order to allow said illumination light generated by said light source to emerge from said optical interface;
said optical assembly being further configured such that a measurement beam path is provided between said optical interface and said detector in order to supply measurement light entering through said optical interface to said detector;
said measurement beam path passing through said aperture of the at least one stray light stop;
said aperture of the at least one stray light stop having a variable diameter;
an actuator;
said controller being configured to control said actuator so as to change the diameter of the aperture, wherein:
said detector is configured to detect light intensity and provide light intensity data; and,
said controller being configured to obtain said light intensity data from said detector and to establish ametropia data representing the ametropia of the eye from said light intensity data and said controller being configured to actuate said actuator on the basis of said ametropia data.

14. The apparatus of claim 12, wherein:
said controller includes at least one of a memory and an interface via which said controller is configured to access a memory;
said memory contains settings data; and,
said controller is configured to calculate at least one of an intended diameter and an intended position of at least one of said first stray light stop and said second stray light stop on the basis of said settings data and said ametropia data and to actuate at least one of said first actuator and said second actuator in such a way that the corresponding one of said diameter corresponds to the intended diameter and said position of the corresponding one of said aperture and said second aperature of said at least one of said first stray light stop and said second stray light stop along said measurement beam path corresponds to the intended position.

15. The apparatus of claim 1, wherein:
said detector is configured to detect light intensity data; and,
said controller is configured to obtain said light intensity data detected by said detector and to establish a component of stray light in the light incident on the detector from said light intensity data and to actuate said first actuator on the basis of said established component of stray light.

16. The apparatus of claim 2, wherein:
said detector is configured to detect light intensity data;
said controller is configured to obtain said light intensity data detected by said detector and to establish a component of stray light in the light incident on the detector from said light intensity data and to actuate at least one of said first actuator and said second actuator on the basis of said established component of stray light.

17. The apparatus of claim 1, wherein said aperture of said first stray light stop is also traversed by said illumination beam path.

18. The apparatus of claim 2, wherein said aperture of said first stray light stop is also traversed by said illumination beam path.

19. The apparatus of claim 1, wherein said aperture of said first stray light stop is not traversed by the illumination beam path.

20. The apparatus of claim 2, wherein said aperture of said first stray light stop is not traversed by the illumination beam path.

21. The apparatus of claim 13, wherein:
said controller includes at least one of a memory and an interface via which said controller is configured to access a memory;
said memory contains settings data; and,
said controller is configured to calculate an intended diameter of the at least one stray light stop on the basis of said settings data and said ametropia data and to actuate said first actuator in such a way that said diameter of the aperture of said at least one stray light stop corresponds to the intended diameter.

22. The apparatus of claim 13, wherein said controller is configured to set said diameter of said aperture such that at least a portion of the light of said light source which is reflected or scattered into the measurement beam path at optical boundary surfaces in said illumination beam path is absorbed by said at least one stray light stop.

23. The apparatus of claim 13, wherein in the case of at least one ametropia of the eye, an intensity of the component of light absorbed by said at least one stray light stop is one of at least 0.3-times, at least 0.6-times and at least 0.9-times the total intensity of the light incident on said detector when said stray light stop is removed from said measurement beam path.

24. The apparatus of claim 13, wherein said detector is configured to detect light intensity data; and
said controller is configured to obtain said light intensity data detected by said detector and to establish a component of stray light in the light incident on the detector from said light intensity data and to actuate said actuator on the basis of said established component of stray light.

* * * * *